(12) United States Patent
Hayashi et al.

(10) Patent No.: US 8,722,942 B2
(45) Date of Patent: *May 13, 2014

(54) METHOD FOR PRODUCING BIPHENYL DERIVATIVE

(75) Inventors: Tamio Hayashi, Shiga (JP); Jiro Nakatani, Shiga (JP)

(73) Assignee: Toray Fine Chemicals Co., Ltd. (JP)

( * ) Notice: Subject to any disclaimer, the term of this patent is extended or adjusted under 35 U.S.C. 154(b) by 842 days.

This patent is subject to a terminal disclaimer.

(21) Appl. No.: 12/377,892

(22) PCT Filed: Oct. 12, 2007

(86) PCT No.: PCT/JP2007/069957
§ 371 (c)(1),
(2), (4) Date: Feb. 18, 2009

(87) PCT Pub. No.: WO2008/047707
PCT Pub. Date: Apr. 24, 2008

(65) Prior Publication Data
US 2010/0230634 A1    Sep. 16, 2010

(30) Foreign Application Priority Data
Oct. 16, 2006 (JP) ................................ 2006-281677

(51) Int. Cl.
*C07C 43/164* (2006.01)
*C07C 17/269* (2006.01)
*C07C 2/84* (2006.01)
*C07C 43/205* (2006.01)
*C07C 17/263* (2006.01)

(52) U.S. Cl.
CPC ......... *C07C 43/2055* (2013.01); *C07C 17/2632* (2013.01); *C07C 2/84* (2013.01)
USPC ........... 568/642; 568/643; 570/182; 570/190; 585/427

(58) Field of Classification Search
CPC .... C07C 43/2055; C07C 17/2632; C07C 2/84
USPC ........... 568/642, 643; 570/182, 190; 585/427
See application file for complete search history.

(56) References Cited

U.S. PATENT DOCUMENTS

| 2,959,596 | A | * | 11/1960 | Ramsden et al. | 549/214 |
| 4,939,309 | A | * | 7/1990 | Puckette | 585/469 |
| 2008/0319238 | A1 | * | 12/2008 | Hayashi et al. | 570/140 |

FOREIGN PATENT DOCUMENTS

| JP | 63295520 A | 12/1988 |
| JP | 2004-256500 A | 9/2004 |

OTHER PUBLICATIONS

Kanth et al., ZnBr2-Catalyzed Efficient Oxidative Homo Coupling of Aryl Magnesium Bromides, Synthetic Communications, vol. 36, 2006, pp. 3079-3084.*
Takashi Nagano et al., "Iron-Catalyzed Oxidative Homo-Coupling of Aryl Grignard Reagents," Organic Letters, 2005, vol. 7, No. 3, pp. 491-493.
Gerard Cahiez et al., "Iron-Catalyzed Homo-Coupling of Simple and Functionalized Arylmanesium Reagents," Organic Letters, 2005, vol. 7, No. 10, pp. 1943-1946.

* cited by examiner

*Primary Examiner* — Rosalynd Keys
(74) *Attorney, Agent, or Firm* — DLA Piper LLP (US)

(57) ABSTRACT

A method produces a biphenyl derivative, with an industrially high yield and excellent productivity, by use of a raw material which is low in cost and toxicity. The method for producing the biphenyl derivative represented by Formula (1) is characterized in that a chlorine atom in a benzene derivative represented by Formula (2) reacts with magnesium metal to convert the benzene derivative into a Grignard reagent, and then the Grignard reagent is subjected to a coupling reaction in the presence of a catalyst and a dichloropropane:

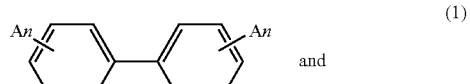

and

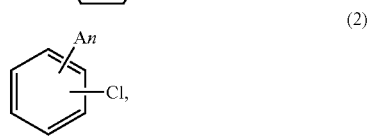

(wherein A represents at least one selected from alkyl groups, alkoxy groups, alkoxymethyl groups, a vinyl group, phenyl groups and chlorine, and n represents an integer of 1 to 4).

6 Claims, No Drawings

METHOD FOR PRODUCING BIPHENYL DERIVATIVE

RELATED APPLICATIONS

This is a §371 of International Application No. PCT/JP2007/069957, with an international filing date of Oct. 12, 2007 (WO 2008/047707 A1, published Apr. 24, 2008), which is based on Japanese Patent Application No. 2006-281677, filed Oct. 16, 2006.

TECHNICAL FIELD

This disclosure relates to a method for producing a biphenyl derivative, and more specifically to an industrially excellent method for producing a biphenyl derivative.

BACKGROUND

Biphenyl derivatives are compounds widely used in fields of organic and polymer chemistry, and, useful compounds in fields that cover wide industrial applications such as fine chemicals, medical and agrochemical raw materials, resins and plastics raw materials, electronic information materials, and optical materials.

Methods for producing biphenyl derivatives are known wherein aromatic halogen compounds are used as a starting substrate. Japanese Patent Application Kokai Publication No. Sho 63-295520 (Examples 1, 3, 4) proposes that a Grignard reagent of an aromatic chloride be reacted with an aromatic bromide in the presence of a nickel catalyst. On the other hand, ORGANIC LETTERS, Vol. 7, No. 3 (2005), 491 493, and ORGANIC LETTERS, Vol. 7, No. (2005), 1943-1946 propose a production method that includes: reacting an aromatic iodide or an aromatic bromide with magnesium to convert them into a Grignard reagent; and then mutually coupling the Grignard reagent under the coexistence of an oxidant by use of the iron chloride (III) catalyst.

However, the method described in Japanese Patent Application Kokai Publication No. Sho 63-295520 (Examples 1, 2, 3, 4) cannot be industrially applied to the case where an aromatic chloride is used as a substrate to be reacted with a Grignard reagent, because the yield of a biphenyl derivative, is low. Moreover, the production methods described in ORGANIC LETTERS, Vol. 7, No. 3 (2005), 491-493, and ORGANIC LETTERS, Vol. 7, No. 10 (2005), 1943-1946 make the produced biphenyl derivative expensive because the methods employ as a stating substrate an aromatic iodide or an aromatic bromide, both of which are highly reactive but expensive. In addition, the oxidants described in ORGANIC LETTERS, Vol. 7, No. 3 (2005), 491-493, and ORGANIC LETTERS, Vol. 7, No. 10 (2005), 1943-1946 are 1,2-dibromoethane and 1,2-dichloroethane, and these belong to Group 2A (material that is probably carcinogenic to humans) and Group 2B (material that possibly carcinogenic to humans), respectively, according to carcinogenic evaluations by International Agency for Research on Cancer (IARC). In particular, 1,2-dichloroethane is specified as a banned substance in Europe.

Industrial use of these materials may cause problems and alternative materials with lower toxicity have been desired.

It could therefore be helpful to provide a method for producing a biphenyl derivative that offers an industrially high yield and is excellent in productivity by use of inexpensive and low toxic raw materials.

SUMMARY

We thus provide methods for producing a biphenyl derivative represented by the following general formula (1), the chlorine atom of a benzene derivative represented by the following general formula (2) is made to react with magnesium metal to convert them into a Grignard reagent, and then two molecules of the Grignard reagent are coupled to each other in the presence of a catalyst and dichloropropane:

Formula 1

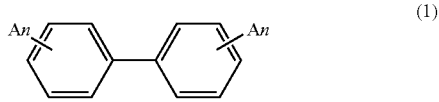
(1)

(wherein A represents at least one selected from alkyl groups, alkoxy groups, alkoxymethyl groups, a vinyl group, phenyl groups and chlorine, and n represents an integer of 1 to 4)

Formula 2

(2)

(wherein A represents at least one selected from alkyl groups, alkoxy groups, alkoxymethyl groups, a vinyl group, phenyl groups, and chlorine, and n represents an integer of 1 to 4).

The method for producing a biphenyl derivative can form a Grignard reagent as an intermediate in a low cost by use of an inexpensive aromatic chloride as a starting substrate and can effectively produce a biphenyl derivative in a high yield by coupling two molecules of the Grignard reagent to each other by use of a low toxic dichloropropane as an oxidant.

DETAILED DESCRIPTION

Our methods will be described in detail below.

The method for producing a biphenyl derivative makes use of the benzene derivative represented by general formula (2) below as a starting substrate:

Formula 2

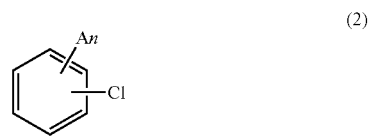
(2)

(wherein A represents at least one selected from alkyl groups, alkoxy groups, alkoxymethyl groups, a vinyl group, phenyl groups, and chlorine, and n represents an integer of 1 to 4).

In the above formula, (2), n is an integer of 1 to 4, preferably 1 or 2. When n is 1 or 2, a more inexpensive starting substrate can be used, and since the reaction effectively proceeds because of few steric reaction inhibiting effect by a substituent in the reaction.

Substituent A is at least one selected from alkyl groups, alkoxy groups, alkoxymethyl groups, a vinyl group, phenyl groups, and chlorine. Specific examples of the alkyl groups include a methyl group, an ethyl group, a normal propyl group, an isopropyl groups, a normal butyl group, and a tertiary butyl group. Specific examples of the alkoxy groups include a methoxy group, an ethoxy group, a normal propoxy group, an isopropoxy group, a normal butoxy group, and a tertiary butoxy group. Specific examples of the alkoxymethyl groups include a methoxy-methyl group, a methoxyethyl group, a methoxy normal propyl group, and a methoxy isopropyl group. The phenyl group may be a non-substituted phenyl group or a substituted phenyl group.

Specific examples of the starting substrate include o-chlorotoluene, m-chlorotoluene, p-chlorotoluene, o-chloroethylbenzene, m-chloroethylbenzene, p-chloroethylbenzene, o-chloro normal propylbenzene, m-chloro normal propylbenzene, p-chloro normal propylbenzene, o-chloro isopropylbenzene, m-chloro isopropylbenzene, p-chloro isopropylbenzene, 3-chloro-o-xylene, 4-chloro-o-xylene, 2-chloro-m-xylene, 4-chloro-m-xylene, 2-chloro-p-xylene, 2-chloro-mesitylene, o-chloroanisole, m-chloroanisole, p-chloroanisole, o-chloro-methoxymethylbenzene, m-chloro-methoxymethylbenzene, p-chloro-methoxymethylbenzene, o-chloro-methoxyethylbenzene, m-chloro-methoxyethylbenzene, p-chloro-methoxyethylbenzene, 2-chloro-biphenyl, 3-chlorobiphenyl, 4-chlorobiphenyl, o-dichlorobenzene, m-dichlorobenzene, p-dichlorobenzene, 1,3,5-trichlorobenzene, 1,2,4-trichlorobenzene. Of these, o-chlorotoluene, m-chlorotoluene, p-chlorotoluene, 4-chloro-o-xylene, p-chloroanisole, p-dichlorobenzene, and p-chloro-methoxy-methylbenzene are preferred.

The chlorine atom of the benzene derivative of the above-mentioned (2) is made to react with the magnesium metal to thereby convert them into a Grignard reagent. The conversion reaction into a Grignard reagent is not particularly limited. However, a well-known conversion reaction can be employed.

Magnesium metal is not particularly limited. However, a powdery metal is preferably used. The conversion reaction into the Grignard reagent is performed in a dehydrated system. The dehydrated solvent is preferably used or an inexpensive Grignard reagent is preferably added to thereby remove water.

In addition, iodine, bromine or inexpensive compounds containing iodine or bromine is preferably added to remove the oxide film on the surface of the magnesium metal and enhance the reactivity of the magnesium metal. The examples of such compounds preferably include methyl iodide, methylbromide, ethyl iodide and ethyl bromide.

In the production method, the catalysts used for coupling reaction between two molecules of the Grignard reagent preferably include Fe, Ag, Cu, Co, Zn, Ni and Pd metals and compounds thereof. The compounds that are preferably used include chlorides, bromides, iodides, fluorides, acetates, acetylacetonate, carbonates, hydroxides and nitrates of these metals. Among these, ferrous chloride (II), ferric chloride (III), ferrous bromide and ferric bromide are preferable.

In addition, the amount of use of the catalyst is preferably from about 0.01 mol % to about 20 mol % based on one mol of the starting substrate, more preferably from about 0.05 mol % to about 10 mol %. The coupling reaction can be performed efficiently and economically by using the amount of the catalyst within the above-mentioned range.

In the production method, dichloropropane is used as an oxidant. The oxidant oxidizes and reproduces the catalyst reduced by the coupling reaction. As a result, the catalytic cycle is repeated, and the reaction yield is improved.

Specific examples of the oxidant includes 1,1-dichloropropane, 1,2-dichloropropane and 1,3-dichloropropane. Of these, 1,2-dichloropropane belongs to Group 3 (materials is not classifiable as to carcinogenicity in humans) according to carcinogenic evaluation by the International Agency for Research on Cancer (IARC). Therefore, 1,2-dichloropropane is preferably used due to toxicity thereof lower than those of the oxidants conventionally proposed. Moreover, the amount of use of the dichloropropane is preferably from 0.1 to 5 times by mole based on one mole of a starting substrate, more preferably 0.2 to 3 times by mole. If the amount of dichloropropane is less than 0.1 times by mole based on the mole of the starting substrate, the effect of catalyst reproduction caused by the oxidant is small. If the amount is more than 5 times by mole, unreacted oxidant remains, whereby a heavy load is needed in isolation refinement of the target material, thus producing inefficiency.

As for a solvent used for the production method, any solvent can be selected so long as it allows the reaction to proceed efficiently. An ethereal solvent in which the Grignard reagent is easily generated is preferred. The specific examples of the solvents include diethyl ether, diisopropyl ether, tetrahydrofuran, N,N-dimethyl formamide, N,N-dimethyl acetamide, N-methylpyrrolidone, 1,3-dioxane, 1,4-dioxane, cyclopropylmethyl ether, methyl-tertiarybutyl ether, ethylene glycol dimethyl ether, diethylene glycol dimethyl ether, triethylene glycol dimethyl ether, tetraethylene glycol dimethyl ether, benzene, toluene, xylene. Of these, diethyl ether, diisopropyl ether, tetrahydrofuran, 1,3-dioxane, 1,4-dioxane, cyclopropylmethyl ether, and methyl-tertiarybutyl ether.

The amount of use of the solvent may be arbitrary according to the solubility of the benzene derivative represented by above formula (2), the Grignard reagent and the product, slurry concentration or the properties of the reaction solution. Preferably, the amount of the solvent is from about 0.5 to about 100 times by mole based on the benzene derivative represented by above formula (2). If the amount is less than about 0.5 times by mole, the yield of the Grignard reagent is decreased. If the amount exceeds about 100 times by mole, the productivity is worsened and the process become non-economical.

In the production method, the reaction temperature of the coupling reaction is preferably from about 30 to about 100° C., more preferably from about 45 to about 70° C. If the reaction temperature is lower than about 30° C., the reaction hardly proceeds. Even if the reaction proceeds, it is likely to stop on the way. In addition, the reaction temperature exceeds about 100° C., the Grignard reagent may decompose before the coupling reaction, and thus is not preferred.

In the production method, during coupling reaction, halogenated biphenyl derivative represented by general formula (3) below are generated as a by-product together with the targeted biphenyl derivative represented by general formula (1) below, whereby a composition containing a biphenyl derivative is obtained:

Formula 1

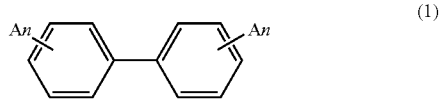

(1)

(wherein A represents at least one selected from alkyl groups, alkoxy groups, alkoxymethyl groups, a vinyl group, phenyl groups, and chlorine, and n represents an integer of 1 to 4)

Formula 3

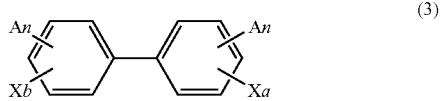

(3)

(wherein A represents at least one selected from alkyl groups, alkoxy groups, alkoxymethyl groups, a vinyl group, phenyl, groups, and chlorine, X represents halogen atom, n represents an integer of 1 to 4, a and b each represent an integer, and the sum of a and b is 1 to 8).

In the composition containing the biphenyl derivative obtained by the production method, the percentage content of the halogenated biphenyl derivative represented by above formula (3) is preferably about 20% by weight or less, more preferably from about 0.01% by weight to about 20% by weight. This is because, when the percentage content of the halogenated biphenyl derivative exceeds about 20% by weight and is used as a raw material for a fine chemical, a medical and agrochemical raw material, a resin and plastics raw material, an electronic information material, and an optical material, or the like, the quality loss of the end-product may be caused. To be more specific, the end-products may have quality problems such as decreased purity, coloring, deteriorated strength, or decreased optical characteristics.

Therefore, it is necessary to reduce, as much as possible, the quantity of by-produced halogenated biphenyl derivative when the target biphenyl derivative is isolated from the coupling reaction solution. The isolation methods include a distillation method, a crystallization method, an extraction method, a column separation method using silica or the like, a simulated moving bed adsorption separation method. Any one of them is acceptable and a plurality of the methods may be used together. Because there is a possibility that activated magnesium and the like remain in the reaction solution, a method of adding water or acidic water to the reaction solution to remove the magnesium salt generated by the reaction into, the aqueous phase and then isolating the biphenyl derivative from the resulting oil phase is preferred. In the distillation method, for instance, although, any one of simple distillation, rectification, vacuum distillation, and atmospheric distillation is acceptable, vacuum distillation is preferably used. The halogenated biphenyl derivative have higher boiling points than the target biphenyl derivative. Thus, the distillation operation needs to be performed such that the target biphenyl derivative is distilled off while the halogenated biphenyl derivative are not distilled off to remain as much as possible in the distillation residue or the like.

In the production method, the percentage content of the halogenated biphenyl derivative in the biphenyl derivative obtained by any one of the isolating methods may be preferably about 0.01% by weight to about 20% by weight, more preferably about 0.01% by weight to about 5% by weight. The qualities such as purity, coloring, strength and optical characteristics of an end-product made from the biphenyl derivative serving as a raw material can be maintained by making the halogenated biphenyl derivative percentage content within the above-mentioned range.

The biphenyl derivative obtained by the production method can be converted into a variety of compounds in a wide range of fields. It is meaningful that the biphenyl derivative can be obtained efficiently and industrially by use of inexpensive raw materials and the oxidant with low toxicity.

EXAMPLES

Our methods will be described in more detail by means of the following examples hereinafter. However, our methods are by no means limited thereto. In addition, manufacturer grades of the reagents used here all correspond to the industrial grade or higher.

Example 1

136.89 grams of tetrahydrofuran (1.90 mol; made by Nacalai Tesque Inc.), 11.5 g of a magnesium powder (0.47 mol; made by Chuo-Kosan Co., Ltd.), and 5 g of o-chlorotoluene (0.008 mol; made by Wako Pure Chemical Industries Ltd.) were placed in a reactor with a thermometer and agitated while substituting the inside of the system by nitrogen. Thereto was added 1 g at tertiary butyl magnesium chloride (0.008 mol; made by Tokyo Chemical Industry Ltd.) and water in the system was removed. Subsequently, 4.3 g of ethyl bromide (0.04 mol; made by Wako Pure Chemical Industries Ltd.) was added thereto. The system was agitated for a while and it was confirmed that heat was generated. Next, 45 g of o-chlorotoluene (0.35 mol) was added dropwise while keeping the temperature of the reaction solution at 35 to 50° C. After dropwise addition, the solution was aged. while agitating at 60° C. for three hours (Grignard reagent yield: 83%).

Next, a catalyst-containing solution was prepared by adding 53.6 g of 1,2-dichloropropane (0.74 mol; made by Wako Pure Chemical Industries Ltd.) to a liquid prepared by addition of 7.1 g, (0.10 mol) of tetrahydrofuran to 1.9 g of iron chloride (III) (0.012 mol; made by Wako Pure Chemical Industries Ltd.). This solution was added dropwise to the above Grignard reagent solution while keeping the reaction solution temperature at 30 to 50° C. and a coupling reaction was performed. After completion of dropwise addition, the reaction was carried out at 50° C. for 3 hours. After completion of the reaction, the reaction solution was cooled and poured into water and the oil phase was extracted with diethyl ether (reagent grade, Nacalai Tesque, Inc.). Thereto was added acetophenone (reagent grade, Nacalai Tesque, Inc.) as an internal standard material and the reaction solution was analyzed by a gas chromatograph (column: made by GL Sciences Inc.; inert cap 1: length 60 m×diameter 0.25 mm, film thickness 0.40 μm). The yield of 2,2'-dimethylbiphenyl relative to the amount of o-chlorotoluene was 84.4%. In addition, the amount of chlorinated 2,2'-dimethylbiphenyls as a by-product were 0.54% by weight to the amount of 2,2'-dimethylbiphenyl.

Example 2

A reaction was carried out similarly to Example 1 except that o-chlorotoluene was changed into m-chlorotoluene. The yield of 3,3'-dimethylbiphenyl relative to the amount of m-chlorotoluene was 79.4%. In addition, the amount of by-produced chlorinated 3,3'-dimethyl-biphenyls were 1.4% by weight relative to the amount of the 3,3'-dimethylbiphenyl.

Example 3

A reaction was carried out similarly to Example 1 except that o-chlorotoluene was changed into p-chlorotoluene. The yield of 4,4'-dimethylbiphenyl relative to the amount of p-chlorotoluene was 82.0%. In addition, the amount of by-produced chlorinated 4,4'-dimethyl-biphenyls were 0.80% by weight relative to the amount of the 4,4'-dimethylbiphenyl.

Example 4

123.1 grams of tetrahydrofuran (1.71 mol; Nacalai Tesque Inc.), 10.4 g of a magnesium powder (0.43 mol; made by Chuo-Kosan Co. Ltd.) and 5 g of 4-chloro-o-xylene (0.036 mol; made by Wako Pure Chemical Industries Ltd.) were placed in a reactor with a thermometer and agitated while substituting the inside of the system by nitrogen. One g of tertiary butyl magnesium chloride (0.008 mol; made by Tokyo Chemical Industry Co. Ltd.) was added thereto, and water in the system was removed. Subsequently, 3.9 g of ethyl bromide (0.04 mol; made by Wako Pure Chemical Industries Ltd.) was added thereto. The system was agitated for a while and it was confirmed that heat was generated. Next, 45 g of 4-chloro-o-xylene (0.32 mol) was added dropwise thereto while keeping the temperature of the reaction solution at 35 to 50° C. After the completion of dropwise addition, the solution was aged while agitating at 60° C. three hours (Grignard reagent yield: 90%).

Next, a catalyst-containing solution was prepared by adding 48.2 g of 1,2-dichloropropane (0.67 mol; made by Wako Pure Chemical Industries Ltd.) to a liquid prepared by addition of 6.4 g of tetrahydrofuran (0.09 mol) to 1.7 g of iron chloride (III) (0.011 mol; Wako Pure Chemical Industries Ltd.). This solution was added dropwise to the above Grignard reagent solution while keeping the reaction solution temperature at 30 to 50° C. and a coupling reaction was performed. After completion of dropwise addition, the reaction was carried out at 50° C. for 3 hours. After completion of the reaction, the reaction solution, was cooled and pored into water and the oil, phase was extracted with diethyl ether (reagent grade, Nacalai Tesque, Inc.). Thereto was added acetophenone (reagent grade, Nacalai Tesque, Inc.) as an internal standard material and the reaction solution was analyzed by a gas chromatograph (column: made by GL Sciences Inc.; inert cap 1: length 60 m×diameter 0.25 mm, film thickness 0.40 μm). The yield of 3,4,3',4'-tetramethylbiphenyl relative to 4-chloro-o-xylene was 72.5%. In addition, the amount of by-produced chlorinated 3,4,3',4'-tetramethylbiphenyls were 1.8% by weight relative to the amount of 3,4, 3'4'-tetramethylbiphenyl.

Example 5

A reaction was carried out similarly to Example 4 except that 4-chloro-o-xylene was changed into 3-chloro-o-xylene. The yield of 2,3,2',3'-tetramethylbiphenyl was 74.3% relative to the amount of 3-chloro-o-xylene. In addition, the amount of by-produced chlorinated 2,3,2',3'-tetramethylbiphenyls were 1.6% by weight relative to the amount of the 2,3,2',3'-tetra-methylbiphenyl.

Comparative Example 1

A reaction was carried out similarly to Example 1 except that the oxidant was changed from 53.6 g of 1,2-dichloropropane (0.74 mol; made by the Wako Pure Chemical Industries Ltd.) to 1,2-chloroethane. The yield of 2,2'-dimethylbiphenyl was 65.9% relative to the amount of 6-chlorotoluene. In addition, the amount of by-produced chlorinated 2,2'-dimethylbiphenyls were 4.5% by weight relative to the amount of the 2,2'-dimethylbiphenyl.

What is claimed is:

1. A method for producing a biphenyl derivative represented by Formula (1), comprising:
reacting a chlorine atom of a benzene derivative represented by formula (2) with magnesium metal at 35 to 60° C. to convert the benzene derivative into a Grignard reagent; and
coupling two molecules of the Grignard reagent with each other in the presence of an Fe catalyst and 1,2-dichloropropane Formula (1)

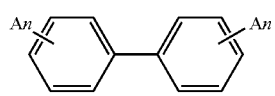

(wherein A represents at least one selected from alkyl groups, alkoxy groups, alkoxymethyl groups, phenyl groups and chlorine, and n represents an integer of 1 to 4)

Formula (2)

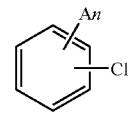

(wherein A represents at least one selected from alkyl groups, alkoxy groups, alkoxymethyl groups, phenyl groups, and chlorine, and n represents an integer of 1 to 4).

2. The method according to claim 1, wherein the n representing the number of the substituent A in Formula (2) is 1 or 2.

3. The method according to claim 2, wherein the Fe catalyst further comprises at least one metal selected from the group consisting of Ag, Cu, Co, Zn, Ni and Pd or at least one compound of metal selected therefrom.

4. The method according to claim 1, further comprising:
purifying the biphenyl derivative so that the content of halogenated biphenyl derivative represented by Formula (3) is from 0.01% by weight to 1.8% by weight:

Formula (3)

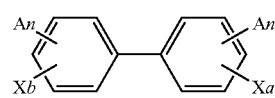

(wherein A represents at least one selected from the group consisting of alkyl groups, alkoxy groups, alkoxymethyl groups, phenyl groups and chlorine, X represents a chlorine atom, n represents an integer of 1 to 4, a and b each represent an integer, and the sum of a and b is from 1 to 8).

5. The method according to claim 2, further comprising:
purifying the biphenyl derivative so that the content of halogenated biphenyl derivative represented by Formula (3) is from 0.01% by weight to 1.8% by weight;

Formula (3)

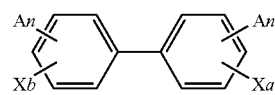

(wherein A represents at least one selected from the group consisting, of alkyl groups, alkoxy groups, alkoxymethyl groups, phenyl groups and chlorine, X represents a chlorine atom, n represents an integer of 1 to 4, a and b each represent an integer, and the sum of a and b is from 1 to 8).

6. The method according to claim 3, further comprising:
purifying the biphenyl derivative so that the content of halogenated biphenyl derivative represented by Formula (3) is from 0.01% by weight to 1.8% by weight:

Formula (3)

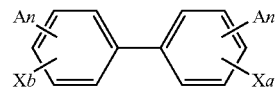

(wherein A represents at least one selected from the group consisting of alkyl groups, alkoxy groups, alkoxymethyl groups, phenyl groups and chlorine, X represents a chlorine atom, n represents an integer of 1 to 4, a and b each represent an integer, and the sum of a and b is from 1 to 8).

\* \* \* \* \*